US011020351B2

(12) United States Patent
Bandi et al.

(10) Patent No.: US 11,020,351 B2
(45) Date of Patent: Jun. 1, 2021

(54) STABLE BILAYER TABLET COMPOSITIONS

(71) Applicant: HETERO LABS LIMITED, Telangana (IN)

(72) Inventors: Parthasaradhi Reddy Bandi, Telangana (IN); Khadgapathi Podile, Telangana (IN); Sunil Deviprasad Tiwari, Telangana (IN); Srinivasa Rao Gella, Telangana (IN)

(73) Assignee: HETERO LABS LIMITED, Hyderabad (IN)

( * ) Notice: Subject to any disclaimer, the term of this patent is extended or adjusted under 35 U.S.C. 154(b) by 108 days.

(21) Appl. No.: 16/103,615

(22) Filed: Aug. 14, 2018

(65) Prior Publication Data
US 2019/0290588 A1 Sep. 26, 2019

(30) Foreign Application Priority Data
Mar. 26, 2018 (IN) .............. 201841011100

(51) Int. Cl.
*A61K 9/20* (2006.01)
*A61K 31/7048* (2006.01)
*A61K 31/522* (2006.01)
*A61K 9/00* (2006.01)

(52) U.S. Cl.
CPC .......... *A61K 9/2086* (2013.01); *A61K 9/2018* (2013.01); *A61K 9/2054* (2013.01); *A61K 31/7048* (2013.01); *A61K 9/0002* (2013.01); *A61K 9/2095* (2013.01); *A61K 31/522* (2013.01); *A61K 2300/00* (2013.01)

(58) Field of Classification Search
CPC .............. A61K 9/2086; A61K 31/7048; A61K 9/2054; A61K 9/2018; A61K 9/2095; A61K 2300/00; A61K 31/522; A61K 9/0002; A61K 9/209
See application file for complete search history.

(56) References Cited

U.S. PATENT DOCUMENTS

| 2016/0000816 A1* | 1/2016 | Broedl ................. A61K 9/2018 514/23 |
| 2017/0165209 A1* | 6/2017 | Baron .................... A61K 31/40 |
| 2018/0251447 A1* | 9/2018 | Collin ...................... A61P 9/04 |

* cited by examiner

*Primary Examiner* — Hasan S Ahmed
(74) *Attorney, Agent, or Firm* — IP Pundit LLC

(57) ABSTRACT

The invention relates to stable bilayer tablet compositions comprising empagliflozin, linagliptin and pharmaceutically acceptable excipients which show no incompatibilities and the compositions having good stability and superior dissolution profile.

10 Claims, No Drawings

STABLE BILAYER TABLET COMPOSITIONS

CROSS REFERENCE TO RELATED APPLICATIONS

This application claims priority to Indian Patent Application No. IN 201841011100, filed on Mar. 26, 2018; the disclosures of all of which are hereby incorporated by reference in their entirety.

FIELD OF THE INVENTION

The invention relates to stable bilayer tablet compositions comprising empagliflozin, linagliptin and pharmaceutically acceptable excipients and process for the preparation of such compositions.

BACKGROUND OF THE INVENTION

Empagliflozin is an orally-active inhibitor of the sodium-glucose co-transporter 2 (SGLT2) known from U.S. Pat. No. 7,579,449. It is chemically D-Glucitol, 1,5-anhydro-1-C-[4-chloro-3-[[4-[[(3S)-tetrahydro-3-furanyl]oxy]phenyl]methyl]phenyl]-, (1S) having structure as below:

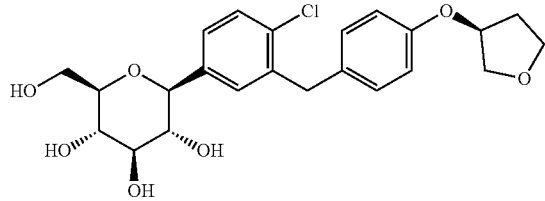 [SMILES: OC[C@H]1O[C@@H](c2ccc(Cl)c(Cc3ccc(O[C@H]4CCOC4)cc3)c2)[C@H](O)[C@@H](O)[C@@H]1O]

Linagliptin is an orally-active inhibitor of the dipeptidyl peptidase-4 (DPP-4) enzyme known from U.S. Pat. No. 7,407,955. It is chemically 1H-Purine-2,6-dione, 8-[(3R)-3-amino-1-piperidinyl]-7-(2-butyn-1-yl)-3,7-dihydro-3-methyl-1-[(4-methyl-2-quinazolinyl) methyl] having structure as below:

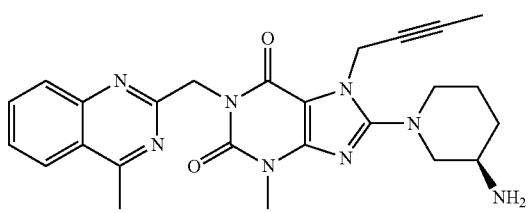 [SMILES: CC#CCn1c(N2CCC[C@@H](N)C2)nc2c1c(=O)n(Cc1nc(C)c3ccccc3n1)c(=O)n2C]

Tablets of empagliflozin in combination with linagliptin for oral administration are currently being marketed in United States under the name Glyxambi® by Boehringer Ingelheim indicated as an adjunct to diet and exercise to improve glycemic control in adults with type 2 diabetes mellitus and are available as single layer tablets in two dosage strengths i.e. 10 mg/5 mg and 25 mg/5 mg respectively.

U.S Patent publication No. 20110014284 describes pharmaceutical compositions comprising empagliflozin, process for the preparation of such compositions and their use in the treatment of various conditions including type 1 diabetes mellitus and type 2 diabetes mellitus.

U.S Patent publication No. 20170312287 (hereinafter '287) describes pharmaceutical compositions of linagliptin, their preparation and their use in the treatment of type 1 diabetes mellitus and type 2 diabetes mellitus.

U.S Patent publication No. 20100209506 (hereinafter '506) claims single layered pharmaceutical compositions comprising combination of empagliflozin and linagliptin.

According to '287 and '506, in attempts to prepare pharmaceutical compositions of linagliptin, it has been observed that linagliptin with a primary or secondary amino group show incompatibilities, degradation problems, or extraction problems with a number of customary excipients. Though the compounds themselves are very stable, they react with many excipients used in solid dosage forms. The amino group appears to react with reducing sugars and with other reactive carbonyl groups and with carboxylic acid functional groups formed for example at the surface of microcrystalline cellulose by oxidation. These unforeseen difficulties are primarily observed in low dosage ranges which are required due to the surprising potency of the selected inhibitors. Thus, pharmaceutical compositions are required to solve these technical problems associated with the unexpected potency of linagliptin.

Hence, there exists a need to develop formulations without compromising on the formulation properties, dissolution profile as well as stability of the formulation.

Inventors of the present invention have prepared stable bilayer tablet compositions comprising empagliflozin, linagliptin and pharmaceutically acceptable excipients. The compositions according to the invention having good stability and superior dissolution profile.

SUMMARY OF THE INVENTION

One aspect of the present invention relates to stable bilayer tablet compositions comprising empagliflozin, linagliptin and pharmaceutically acceptable excipients.

Another aspect of the present invention is a stable bilayer tablet composition comprising 10 mg to 25 mg of empagliflozin, 5 mg of linagliptin and pharmaceutically acceptable excipients thereof, wherein empagliflozin is present in an amount of 1-20% (w/w) and linagliptin is present in an amount of 1-10% (w/w) based on total weight of the composition.

Another aspect of the present invention is a stable bilayer tablet composition comprising 10 mg of empagliflozin, 5 mg of linagliptin and pharmaceutically acceptable excipients thereof, wherein empagliflozin is present in an amount of 3-10% (w/w) and linagliptin is present in an amount of 1-6% (w/w) based on total weight of the composition.

Another aspect of the present invention is a stable bilayer tablet composition comprising 25 mg of empagliflozin, 5 mg of linagliptin and pharmaceutically acceptable excipients thereof, wherein empagliflozin is present in an amount of 8-16% (w/w) and linagliptin is present in an amount of 1-6% (w/w) based on total weight of the composition.

Another aspect of the present invention is a stable bilayer tablet composition comprising empagliflozin, linagliptin and pharmaceutically acceptable excipients such as microcrystalline cellulose, lactose monohydrate and croscarmellose sodium which shows no incompatibilities and the composition having good stability and superior dissolution profile.

Another aspect of the present invention is a stable bilayer tablet composition comprising empagliflozin, linagliptin, 5-30% (w/w) of microcrystalline cellulose, 10-40% (w/w) of lactose monohydrate and 0.5-5% (w/w) of croscarmellose sodium based on total weight of the composition.

Another aspect of the present invention is a stable bilayer tablet composition comprising empagliflozin, linagliptin, 10-25% (w/w) of microcrystalline cellulose, 20-30% (w/w) of lactose monohydrate and 0.5-5% (w/w) of croscarmellose sodium based on total weight of the composition.

Another aspect of the present invention is a stable bilayer tablet composition comprising 1-20% (w/w) of empagliflozin, 1-10% (w/w) of linagliptin, 5-30% (w/w) of microcrystalline cellulose, 10-40% (w/w) of lactose monohydrate and 0.5-5% (w/w) of croscarmellose sodium based on total weight of the composition.

Yet another aspect of the present invention is a stable bilayer tablet composition comprising 10 mg to 25 mg of empagliflozin, 5 mg of linagliptin and pharmaceutically acceptable excipients which shows no incompatibilities and having good stability, superior dissolution profile and the composition having not more than 0.2% of any single impurity and not more than 1% of total impurities.

The details of one or more embodiments of the present invention are set forth in the description below. Other features, objects and advantages of the invention will be apparent from the description.

DETAILED DESCRIPTION OF THE INVENTION

The present invention relates to stable bilayer tablet compositions comprising empagliflozin, linagliptin and pharmaceutically acceptable excipients.

The term "composition" as used herein refers to a dosage form suitable for oral administration, such as tablets, granules, powder, spheroids, pellets, pills, capsule, solution, suspension, emulsion and the like.

The term "bilayer tablet" as used herein refers to a coated or uncoated tablet with two layers of different materials compressed together wherein each layer having same or different release profiles.

The term "stable bilayer tablet" as used herein refers to a bilayer tablet with not more than 0.2% of any single impurity and not more than 1% of total impurities.

The term "pharmaceutically acceptable" as used herein means that which is useful in preparing a pharmaceutical composition that is generally safe and non-toxic.

The term "excipients" as used herein means a component of a pharmaceutical product that is not an active ingredient such as, for example, diluents, binders, carriers and the like. The excipients that are useful in preparing a pharmaceutical composition are generally safe and non-toxic.

One embodiment of the present invention is a stable bilayer tablet composition comprising 10 mg to 25 mg of empagliflozin, 5 mg of linagliptin and pharmaceutically acceptable excipients thereof, wherein empagliflozin is present in an amount of 1-20% (w/w) and linagliptin is present in an amount of 1-10% (w/w) based on total weight of the composition.

Another embodiment of the present invention is a stable bilayer tablet composition comprising 10 mg of empagliflozin, 5 mg of linagliptin and pharmaceutically acceptable excipients thereof, wherein empagliflozin is present in an amount of 3-10% (w/w) and linagliptin is present in an amount of 1-6% (w/w) based on total weight of the composition.

Another embodiment of the present invention is a stable bilayer tablet composition comprising 25 mg of empagliflozin, 5 mg of linagliptin and pharmaceutically acceptable excipients thereof, wherein empagliflozin is present in an amount of 8-16% (w/w) and linagliptin is present in an amount of 1-6% (w/w) based on total weight of the composition.

The present invention provides a stable bilayer tablet composition comprising empagliflozin, linagliptin and pharmaceutically acceptable excipients comprising one or more of fillers, binders, disintegrants, lubricants, glidants and the like.

Suitable fillers include, but are not limited to starch, dibasic calcium phosphate, tribasic calcium phosphate, microcrystalline cellulose, calcium carbonate, dextrose, kaolin, magnesium carbonate, magnesium oxide, lactose monohydrate, sugar alcohols such as mannitol, sorbitol, erythritol and the like and combinations thereof. Preferred fillers are microcrystalline cellulose, lactose monohydrate, mannitol and combinations thereof.

Suitable binders include, but are not limited to carbomers, dextrin, ethyl cellulose, hydroxypropyl cellulose, povidone, copovidone, gelatin, polymethacrylates, pregelatinized starch, sodium alginate, gums, synthetic resins, silicic acid and the like and combinations thereof. Preferred binders are hydroxypropyl cellulose, copovidone and combinations thereof.

Suitable disintegrants include, but are not limited to croscarmellose sodium, sodium starch glycolate, crospovidone, polacrillin potassium, microcrystalline cellulose, carboxymethyl cellulose calcium, starches such as corn starch, potato starch, pre-gelatinized starch and modified starches, clays, bentonite, and the like and combinations thereof. Preferred disintegrants are croscarmellose sodium, corn starch and combinations thereof.

Suitable lubricants include, but are not limited to calcium stearate, glyceryl monostearate, glyceryl palmitostearate, hydrogenated castor oil, hydrogenated vegetable oil, light mineral oil, magnesium stearate, mineral oil, polyethylene glycol, sodium benzoate, sodium lauryl sulfate, sodium stearyl fumarate, stearic acid, talc, zinc stearate, and the like and combinations thereof. Preferred lubricant is magnesium stearate.

Suitable glidants include, but are not limited to colloidal silicon dioxide, talc, starch, starch derivatives, and the like and combinations thereof. Preferred glidant is colloidal silicon dioxide.

Another embodiment of the present invention is a stable bilayer tablet composition comprising empagliflozin, linagliptin and pharmaceutically acceptable excipients such as microcrystalline cellulose, lactose monohydrate and croscarmellose sodium which shows no incompatibilities and the composition having good stability and superior dissolution profile.

Another embodiment of the present invention is a stable bilayer tablet composition comprising empagliflozin, linagliptin, 5-30% by weight of microcrystalline cellulose, 10-40% (w/w) of lactose monohydrate and 0.5-5% (w/w) of croscarmellose sodium based on total weight of the composition.

Another embodiment of the present invention is a stable bilayer tablet composition comprising empagliflozin, linagliptin, 10-25% by weight of microcrystalline cellulose, 20-30% (w/w) of lactose monohydrate and 0.5-5% (w/w) of croscarmellose sodium based on total weight of the composition.

Another embodiment of the present invention is a stable bilayer tablet composition comprising 1-20% (w/w) of empagliflozin, 1-10% (w/w) of linagliptin, 5-30% (w/w) of microcrystalline cellulose, 10-40% (w/w) of lactose monohydrate and 0.5-5% (w/w) of croscarmellose sodium based on total weight of the composition.

Another embodiment of the present invention is a stable bilayer tablet composition comprising empagliflozin and linagliptin exhibits dissolution of more than 85% of empagliflozin and linagliptin within 15 minutes in a dissolution test using USP paddle type dissolution apparatus.

Another embodiment of the present invention is a stable bilayer tablet composition comprising 10 mg to 25 mg of empagliflozin, 5 mg of linagliptin and pharmaceutically acceptable excipients which shows no incompatibilities and having good stability, superior dissolution profile and the composition having not more than 0.2% of any single impurity and not more than 1% of total impurities.

The stable bilayer tablet compositions mentioned herein are in the form of immediate release tablets and are prepared by dry granulation, wet granulation or direct compression, preferably, wet granulation.

The stable bilayer tablet compositions were prepared by making two separate granulations containing empagliflozin in one granulation and linagliptin in other granulation, Empagliflozin and/or linagliptin and other excipients, in particular one or more diluents, one or more disintegrants are premixed and granulated with the binder solution, for example using a high shear granulator. The wet granulation step is usually followed by one or more drying and sieving steps. Glidants and lubricants are blended with the dried granules. Suitable bilayer compression machine was used to compress the empagliflozin layer followed by linagliptin layer with suitable tooling and finally the bilayer tablets were film coated.

The stable bilayer tablet compositions of empagliflozin and linagliptin of the present invention can be used as an adjunct to diet and exercise to improve glycemic control in adults with type 2 diabetes mellitus.

EXAMPLES

Certain specific aspects and embodiments of this invention are described in further detail by the examples below, which are provided only for purposes of illustration and are not intended to limit the scope of the invention in any manner.

Example 1

Bilayer tablet composition comprising empagliflozin and linagliptin:

TABLE 1

| Ingredients | mg/unit | mg/unit |
| --- | --- | --- |
| First layer: | | |
| Empagliflozin | 10.00 | 25.00 |
| Microcrystalline cellulose | 25.00 | 25.00 |
| Lactose monohydrate | 60.50 | 45.50 |
| Croscarmellose sodium | 4.50 | 4.50 |
| Hydroxypropyl cellulose | 1.00 | 1.00 |
| Purified water | Qs | Qs |
| Extra granular | | |
| Colloidal silicon dioxide | 1.00 | 1.00 |
| Magnesium stearate | 1.00 | 1.00 |
| Second layer: | | |
| Linagliptin | 5.00 | 5.00 |
| Mannitol | 72.50 | 72.50 |
| Corn starch | 6.00 | 6.00 |
| Croscarmellose sodium | 2.00 | 2.00 |
| Copovidone | 10.00 | 10.00 |
| Purified water | Qs | Qs |

TABLE 1-continued

| Ingredients | mg/unit | mg/unit |
| --- | --- | --- |
| Extra granular | | |
| Magnesium stearate | 1.50 | 1.50 |
| Core tablet weight (First layer + Second layer) | 200.00 | 200.00 |
| Film coating material weight | 5.00 | 5.00 |
| Total weight of coated tablet | 205 | 205 |

Brief Manufacturing Process:

Empagliflozin Layer:

1. Empagliflozin, lactose monohydrate, croscarmellose sodium and microcrystalline cellulose were sifted through mesh #40.

2. Materials of step no. 1 were blended for 15 minutes using a suitable blender.

3. Binder solution was prepared by slowly adding hydroxypropyl cellulose to purified water under continuous stirring until clear solution was obtained.

4. Granulate the blend of step no. 2 with binder solution of step no. 3 to obtain suitable granules.

5. Wet granules of step no. 4 were dried in a suitable dryer at 60±5° C., drying continued to get desired LOD range.

6. Dried granules of step no. 5 were passed through mesh #24.

7. Colloidal silicon dioxide was sifted through mesh #40,

8. Dried granules of step no. 6 were loaded in to suitable blender and colloidal silicon dioxide of step no. 7 was added and blended for 15 minutes, 9. Magnesium stearate was sifted through suitable mesh, 10. Magnesium stearate of step no. 9 was added to the blend of step no. 8 and blended for 5 minutes.

Linagliptin Layer:

1. Linagliptin, corn starch, croscarmellose sodium and mannitol were sifted through suitable mesh, 2. Materials of step no. 1 were blended for 15 minutes using a suitable blender.

3. Binder solution was prepared by slowly adding copovidone to purified water under continuous stirring until clear solution was obtained.

4. Granulate the blend of step no. 2 with binder solution of step no. 3 to obtain suitable granules.

5. Wet granules of step no. 4 were dried in a suitable dryer at 60±5° C., drying continued to get desired LOD range.

6. Dried granules of step no. 5 were passed through mesh #24.

7. Materials of step no. 6 was loaded into suitable blender and blended for 15 minutes.

8. Magnesium stearate was sifted through suitable mesh.

9. Magnesium stearate of step no. 8 was added to the materials of step no. 7 and blended for 5 minutes.

Compression:

Suitable bilayer compression machine was used to compress the empagliflozin layer followed by linagliptin layer with suitable tooling and finally the bilayer tablets were film coated.

Example 2

TABLE 2

| Ingredients | mg/unit | mg/unit |
|---|---|---|
| First layer: | | |
| Empagliflozin | 10.00 | 25.00 |
| Microcrystalline cellulose | 34.00 | 34.00 |
| Lactose monohydrate | 40.50 | 35.50 |
| Croscarmellose sodium | 4.50 | 1.50 |
| Hydroxypropyl cellulose | 1.00 | 1.00 |
| Extra granular | | |
| Colloidal silicon dioxide | 1.50 | 1.50 |
| Magnesium stearate | 1.50 | 1.50 |
| Second layer: | | |
| Linagliptin | 5.00 | 5.00 |
| Mannitol | 40.50 | 33.50 |
| Corn starch | 6.00 | 6.00 |
| Croscarmellose sodium | 2.00 | 2.00 |
| Copovidone | 8.00 | 8.00 |
| Extra granular | | |
| Magnesium stearate | 1.50 | 1.50 |
| Core tablet weight (First layer + Second layer) | 156 | 156 |
| Film coating material weight | 5.00 | 5.00 |
| Total weight of coated tablet | 161 | 161 |

Manufacturing Process:

Bilayer tablet composition of example 2 was prepared using standard dry granulation method (roller compaction).

Example 3

TABLE 3

| Ingredients | mg/unit | mg/unit |
|---|---|---|
| First layer: | | |
| Empagliflozin | 10.00 | 25.00 |
| Microcrystalline cellulose | 16.10 | 16.10 |
| Lactose monohydrate | 32.20 | 29.20 |
| Croscarmellose sodium | 3.22 | 3.22 |
| Hydroxypropyl cellulose | 1.00 | 1.00 |

TABLE 3-continued

| Ingredients | mg/unit | mg/unit |
|---|---|---|
| Colloidal silicon dioxide | 0.97 | 0.97 |
| Magnesium stearate | 1.61 | 1.61 |
| Second layer: | | |
| Linagliptin | 5.00 | 5.00 |
| Mannitol | 32.40 | 32.40 |
| Corn starch | 2.00 | 2.00 |
| Croscarmellose sodium | 2.00 | 2.00 |
| Copovidone | 8.00 | 13.00 |
| Magnesium stearate | 1.50 | 1.50 |
| Core tablet weight (empagliflozin layer + linagliptin layer) | 116 | 133 |
| Film coating material weight | 5.00 | 5.00 |
| Total weight of coated tablet | 121 | 138 |

Manufacturing Process:

Bilayer tablet composition of example 3 was prepared using standard direct compression method.

Dissolution Test:

The standard dissolution test is described in USP31-NF26 S2, chapter 711 (dissolution). The paddle method (apparatus 2) with an agitation speed of 50 rpm was used. The dissolution media is 900 mL 0.05 M Potassium phosphate buffer pH 6.8 at a temperature of 37° C. Samples were taken after 10, 15, 20, 30 and 45 minutes. The samples were analyzed via HPLC method.

TABLE 4

Dissolution profile of bilayer tablets according to the example 1:

| Time | 10 mg/5 mg | | 25 mg/5 mg | |
|---|---|---|---|---|
| in Min | Empagliflozin | Linagliptin | Empagliflozin | Linagliptin |
| 10 | 87 | 93 | 89 | 86 |
| 15 | 91 | 100 | 93 | 89 |
| 20 | 92 | 101 | 94 | 91 |
| 30 | 93 | 102 | 95 | 94 |
| 45 | 94 | 102 | 95 | 95 |

The stability can be tested in standard tests, for example after 3 months storage at 40° C. and 75% relative humidity. The tablets were packed in HDPE container with 2 gm silica gel.

TABLE 5

Stability data: Example 1

| | Condition & Storage period 40° C./75% RH | | | |
|---|---|---|---|---|
| | Initial | | 3 Months | |
| | Empagliflozin | Linagliptin | Empagliflozin | Linagliptin |
| Assay (% w/w) | 96.6 | 96.8 | 98.7 | 102.3 |
| Water content (% w/w) | 4.05 | | 3.25 | |
| Impurities: | | | | |
| (2S,3R,4R,5S,6R)-2-(4-chloro-3-(4-hydroxybenzyl)phenyl)-6-(hydroxymethyl)tetrahydro-2H-pyran-3,4,5-triol | 0.000 | | 0.00 | |

TABLE 5-continued

Stability data:
Example 1

| | Condition & Storage period 40° C./75% RH | | | |
|---|---|---|---|---|
| | Initial | | 3 Months | |
| | Empagliflozin | Linagliptin | Empagliflozin | Linagliptin |
| (3R)-tetrahydro-3-furanyl-4-methylbenzenesulfonate | | 0.008 | | 0.010 |
| (2S,3S,4R,5R,6R)-2-(3-(4-Acetoxybenzyl)-4-chlorophenyl)-6-(acetoxymethyl tetrahydro-2H-pyran-3,4,5-triyl triacetate | 0.000 | | 0.000 | |
| 8-Bromo-7-(but-2-ynyl)-3-methyl-1-((4-methylquinazolin-2-yl)methyl)-1H-purine-2,6(3H,7H)-dione | | 0.028 | | 0.018 |
| (R)-7-(but-2-yn-1-yl)-3-methyl-1-((4-methylquinazolin-2-yl)methyl)-8-(piperidin-3-ylamino)-3,7-dihydro-1H-purine-2,6-dione | | 0.004 | | 0.000 |
| MSUI (Maximum Single Unknown Impurity) | 0.059 | | 0.093 | |
| TUI (Total Unknown Impurities) | 0.059 | | 0.160 | |
| Total impurities | 0.158 | | 0.281 | |

We claim:

1. A stable bilayer tablet composition comprising:
   (i) a first layer consisting of 10 mg to 25 mg of empagliflozin and at least one pharmaceutically acceptable excipient;
   (ii) a second layer consisting of 5 mg of linagliptin and at least one pharmaceutically acceptable excipient; and
   (iii) at least one pharmaceutically acceptable excipient;
   wherein the amount of empagliflozin is 1% to 20% (w/w) based on total weight of the composition and the amount of linagliptin is 1% to 10% (w/w) based on total weight of the composition.

2. The composition according to claim 1, comprising:
   (i) a first layer consisting of 10 mg of empagliflozin and at least one pharmaceutically acceptable excipient;
   (ii) a second layer consisting of 5 mg of linagliptin and at least one pharmaceutically acceptable excipient; and
   (iii) at least one pharmaceutically acceptable excipient;
   wherein the amount of empagliflozin is 3% to 10% (w/w) based on total weight of the composition and the amount of linagliptin is 1% to 6% (w/w) based on total weight of the composition.

3. The composition according to claim 1, comprising:
   (i) a first layer consisting of 25 mg of empagliflozin and at least one pharmaceutically acceptable excipient;
   (ii) a second layer consisting of 5 mg of linagliptin; and at least one pharmaceutically acceptable excipient; and
   (iii) at least one pharmaceutically acceptable excipient;
   wherein the amount of empagliflozin is 8% to 16% (w/w) based on total weight of the composition and the amount of linagliptin is 1% to 6% (w/w) based on total weight of the composition.

4. The composition according to claim 1, wherein the at least one pharmaceutically acceptable excipient in the first layer and/or the second layer is selected from the group consisting of microcrystalline cellulose, lactose monohydrate, and croscarmellose sodium.

5. A stable bilayer tablet composition comprising:
   (i) a first layer consisting of empagliflozin and at least one pharmaceutically acceptable excipient;
   (ii) a second layer consisting of linagliptin and at least one pharmaceutically acceptable excipient;
   (iii) 5% to 30% (w/w) of microcrystalline cellulose;
   (iv) 10-40% (w/w) of lactose monohydrate; and
   (v) 0.5% to 5% (w/w) of croscarmellose sodium based on total weight of the composition.

6. The composition according to claim 5, wherein
   (i) the microcrystalline cellulose is present in a total amount of 10% to 25% (w/w) based on total weight of the composition; and
   (ii) the lactose monohydrate is present in a total amount of 20% to 30% (w/w) based on total weight of the composition.

7. The composition according to claim 1, wherein the composition exhibits dissolution of more than 85% of empagliflozin and linagliptin within 15 minutes in a dissolution test using USP paddle type dissolution apparatus.

8. The composition according to claim 1, wherein the composition is an immediate release tablet.

9. The composition according to claim 1, wherein the composition is prepared by wet granulation method.

10. A stable bilayer tablet composition comprising:
    (i) a first layer consisting of 10 mg to 25 mg of empagliflozin and at least one pharmaceutically acceptable excipient; and
    (ii) a second layer consisting of 5 mg of linagliptin and at least one pharmaceutically acceptable excipient;
    wherein the composition comprises no more than 0.2% of any single impurity and no more than 1% of total impurities.

* * * * *